United States Patent [19]

Palmer

[11] Patent Number: 4,820,272

[45] Date of Patent: Apr. 11, 1989

[54] NON-REUSABLE HYPODERMIC SYRINGE

[76] Inventor: Michele M. Palmer, Hummelwaldstr. 10-12, CH 8645 Jona, Switzerland

[21] Appl. No.: 92,047

[22] Filed: Sep. 2, 1987

[51] Int. Cl.⁴ .............................................. A61M 5/00
[52] U.S. Cl. ................................... 604/110; 604/218; 604/220
[58] Field of Search ........................ 604/110, 218, 220

[56] References Cited

U.S. PATENT DOCUMENTS

| 4,367,738 | 1/1983 | Legendre et al. | 604/218 X |
| 4,391,272 | 7/1983 | Stampfli | 604/110 |
| 4,650,468 | 3/1987 | Jennings, Jr. | 604/110 |

Primary Examiner—John D. Yasko
Attorney, Agent, or Firm—Handal & Morofsky

[57] ABSTRACT

A non-reusable hypodermic syringe which comprises a cylinder and a plunger, spaced from the lower end portion of the cylinder there is provided a first half of a one-directional retention means. The plunger comprises a shaft and a piston attached to an end of the shaft, and the second half of the retention means is provided on the shaft close to the connection of the piston. The retention means allows the full insertion of the plunger in the cylinder but impedes its withdrawal. Preferably, a projection ring is provided just above the retention means on the inner cylinder wall that indicates to the user that further movement to insert the plunger will positively engage the retention means. This projection ring acts as a tactile warning to the user to prevent "accidental" engagement of the retention means when filling the syringe. In a preferable embodiment, the upper portion of the cylinder is provided with a further first half of the retention means which prevents any removal of the plunger when inserted in the cylinder.

10 Claims, 1 Drawing Sheet

U.S. Patent  Apr. 11, 1989  4,820,272
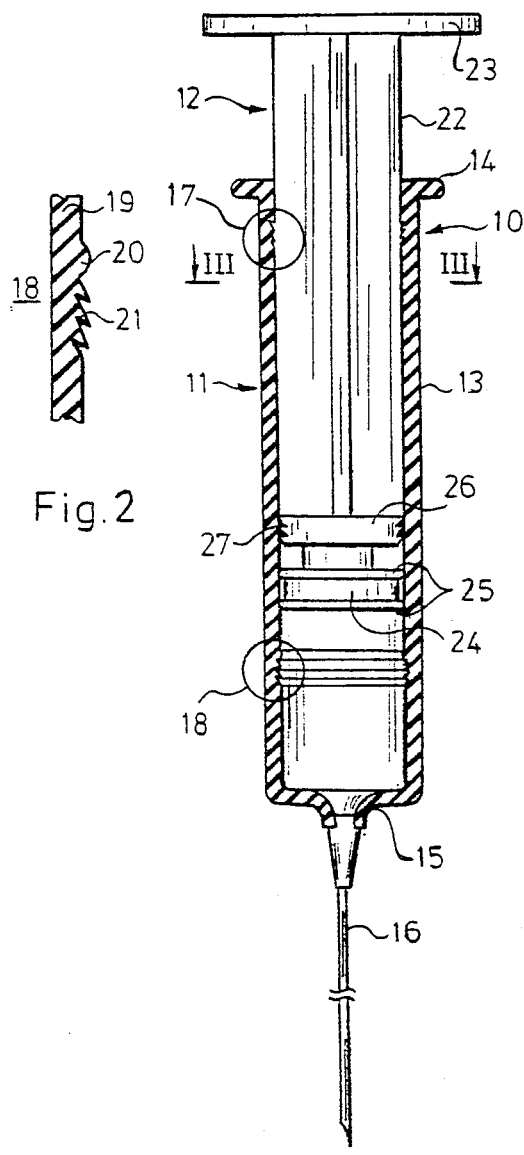
Fig.1
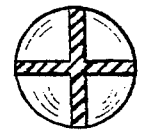
Fig.2
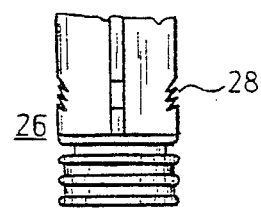
Fig.3
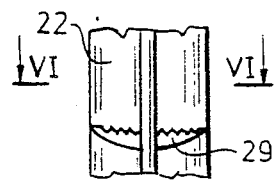
Fig.4
Fig.5
Fig.6

NON-REUSABLE HYPODERMIC SYRINGE

The present invention relates to a non-reusable hypodermic syringe which comprises a cylinder with an open upper end and a substantially closed lower end to which a hypodermic needle can be attached.

There are several types of disposable or so-called non-reusable hypodermic syringes. In expert hands such syringes are discarded after use and there is no danger of a possible contagion owing to multiple use. In recent times the population is becoming more and more cautious concerning their health and any possible contagion. This fear applies in an increased manner to anything connected with direct contact with blood, since some of the most fearful modern diseases can be obtained by direct contact with someone else's blood.

The expert use of hypodermic syringes can not always be guaranteed. There exists a non-negligable small portion of the population who administers injections to themselves and due to economic reasons they incline using disposable syringes several times.

There have been numerous proposals for physically non-reusable hypodermic syringes, in which the withdrawal of the plunger was effectively blocked once it has been fully inserted.

Typical examples of such non reusable syringes are described in U.S. Pat. Nos. 3,998,224 and 4,391,273 both issued to M. Chiquiar-Arias. In these patents the closed lower end of the cylinder was pierced by the plunger in its end position to render any further use impossible. Additionally a snap engagement of the side of the piston with a projection in the cylinder wall blocked any displacement of the plunger in the end position.

Another way of escaping the protection offered by such a syringe is to replace the self-destructing plunger with a standard other type.

Although such a syringe can effectively prevent any further use once the plunger has been fully inserted, a determined desire for further use can, however, render this protection ineffective by not inserting the plunger fully during first use.

The basic objective of the present invention is to provide a more reliable non-reusable hypodermic syringe.

A further objective is to provide a hypodermic syringe in which even the plunger can not be changed with an other one when it has been inserted in the cylinder.

It has been recognised that a more reliable non-reusable hypodermic syringe can be made if a one way movement of the plunger in the syringe is allowed, while the opposite movement is blocked. This "one-way retention" should act somewhere else than the fully inserted zone since such full insertion can well be avoided by a determined user. It has been found that an engagement zone can be provided in about one third of the cylinder from the end position. The filling of the syringe can well be done under such conditions, however, when the vaccination takes place the user should push the plunger sufficiently deep if he wishes to fully utilize the vaccine.

It has also been recognised, according to the the invention, that a similar retention can be made already at the upper end of the cylinder, which will not allow the full release of the plunger from the cylinder. In other words, once the plunger has been inserted into the cylinder, it can not be removed.

The invention will now be described in connection with preferable embodiments thereof, in which reference will be made to the accompanying drawings. In the drawing:

FIG. 1 is a sectional elevation view of a first embodiment of the syringe according to the invention;

FIG. 2 is an enlarged view of the section of the cylinder wall in engagement zones 17 or 18 of FIG. 1;

FIG. 3 is a sectional top view along line III—III of FIG. 1;

FIG. 4 is a portion of an alternative embodiment of the engagement member 26 of the shaft.

FIG. 5 is similar to FIG. 4 for a further alternative embodiment; and

FIG. 6 is a sectional top view along line VI—VI of FIG. 5.

FIG. 1 shows generally a hypodermic syringe 10 that comprises two main elements such as cylinder 11 and plunger 12. The cylinder 11 can be made of a conventional plastic mold and comprises cylindrical portion 13, upper fringe 14 and attachment member 15 at the lower end. The attachment member 15 is connected to hypodermic needle 16 by means of fixed or releasable connection.

The cylindrical portion 13 defines a substantially cylindrical inner wall which has upper and lower engagement zones 17 and 18 respectively. The two zones can be designed similarly and the profile of a preferable embodiment can be seen in the enlarged view of FIG. 2. Wall 19 of the cylinder comprises inwardly projecting ring 20 at upper portions of the zones and below the ring 20 a plurality of downwardly slanted teeth 21 is provided. The lower engagement zone 18 is provided about one third of the height of the cylinder 11 so that the effective volume therebelow for receiving vaccine is at least about one milliliter. The upper engagement zone 17 is provided closely below the upper fringe 14.

Plunger 12 comprises comprises shaft 22 with crosslike cross-section as shown in FIG. 3, thrust plate 23 attached to the upper end of the shaft and formed integrally therewith. Piston 24 is attached to the lower end of the shaft 22. Piston 24 is made by a flexible material such as rubber and comprises two or more spaced sealing rings 25 that smoothly engage the inner wall 19 of the cylinder. Engagement member 26 is provided on the shaft 22 adjacent to the upper end of the piston 24. The main task of the engagement member 26 in cooperation with the engagement zones 17, 18 on the cylinder 11 is to allow the insertion of the plunger below them and to block the removal thereof once the engagement member 26 passed downwardly over any of the zones. To this end the embodiment of the engagement member 26 shown in FIG. 1 has a cylindrical form and a plurality of detention rings 27 with thin upwardly directed edges are provided around the mantle faces of the member 26.

The use of the hypodermic syringe according to the invention is as follows.

Immediately before use the plunger 12 should be inserted in the cylinder 11. At the beginning of this insertion the engagement member 26 on the lower end of the plunger 12 passes over the upper engagement zone 17. The extent of projection of the ring 20 is such that it allows the insertion, however, a predetermined axial force should be exerted on the plunger which deforms the resilient material of the cylinder to allow the introduction of the plunger. When this has happened, the plunger cannot be removed from the cylinder any more, since the upwardly facing detention rings 27 engage the oppositely slanted detention rings 21 in the upper engagement zone. The retention force offered by the engagement of the two oppositely slanted rings is sufficient to prevent the removal of the plunger. The existence of the inwardly projecting ring 20 is to provide a tactible warning to the user that if he proceeds with pushing the plunger in the cylinder, then the engagement will start to work and the plunger cannot be removed again.

When the plunger is inserted and the engagement member 26 is between the two zones 17 and 18, the syringe can be filled with vaccine in a conventional way. The plunger can be inserted until the engagement zone abuts the inwardly projecting upper ring 20 of the lower engagement zone 18. In this position the piston 24 has passed or is engaging the lower engagement zone. Owing to the resilient material of the piston the lower engagement zone is ineffective for the retention of the piston. In this lower abutting position there remains some volume of air below the piston, this can not block the sucking of sufficient amount of vaccine in the syringe. When the syringe is filled with vaccine, the remaining air is released by holding the syringe in upright position and the vaccination can take place. When the plunger is pushed in during use, the slight resistance force of the lower projection ring 20 can be slightly overcome and the piston is pushed till abutting position i.e. when the cylinder is emptied. After this operation the plunger cannot be withdrawn for a further filling, since the lower engagement zone 18 retains the engagement member 26 at the lower end section of the cylinder.

If someone wished to misuse the syringe, he could not empty the cylinder, and at least one milliliter of precious vaccine would remain therein. In addition to the fact that this can be a loss of vaccine material, the remaining (or residual) vaccine would prevent any kind of re-fill and re-use.

This basic mode of operation can be attained with other design of the engagement zones 17, 18 and of the engagement member 26 shown heretofore.

In the embodiment of FIG. 3 the engagement zone consists of for set of upwardly directed teeth 28 made in the cross-ribs of the shaft. The teeth 28 tend to project slightly out of the plane of the edge of the ribs, therefore they abut first the ring 20 thereafter slide over the teeth 21 and being retained there when someone tries to withdraw the plunger.

In a further embodiment shown in FIGS. 5 and 6 the engagement member is formed by serrated and recessed ring 29. The periphery of the ring 29 is sharp, the recessed design permits the ring to be slightly shrunk when being inserted downwardly, however, during an opposite movement the serrated teeth engage the tooth 21 in the cylinder wall and block any further removal.

The presence of the inwardly projecting ring 20 in the upper and lower zones is preferable, however, basically the same operation can be realized without such ring or abutment member.

I claim:

1. A non-reusable hypodermic syringe, comprising:
   (a) a cylinder comprising a resilient material open at one end and substantially closed at the other end;
   (b) a hollow member attached to said closed end and defining an internal duct communicating with the interior of said cylinder, said hollow member being configured and dimensioned to have a hypodermic needle affixed to it;
   (c) a plunger comprising a shaft and a piston attached to an end of said shaft, said piston fitting to the interior of said cylinder, said cylinder defining an engagement zone in a region close to but spaced from said closed end;
   (d) retention means positioned on the interior of said cylinder in said engagement zone;
   (e) a projecting member positioned in said engagement zone at a point further from said closed end than said retention means, said projecting member dimensioned and configured to cause slight yet noticeable hindrance in the motion of the plunger to give a tactile indication of said plunger's proximity to said retention means;
   (f) an engagement member mating with said retention means and positioned on said shaft adjacent to said piston, said engagement member cooperating with said retention means to allow insertion of said member in said cylinder into said engagement zone and to prevent withdrawal thereof.

2. The syringe as claimed in claim 1, wherein said retention means comprising a plurality of rings having downwardly slanted edges facing the interior of said cylinder.

3. The syringe as claimed in claim 2, wherein said engagement member comprising upwardly directed teeth cooperating with said edges when said plunger being withdrawn.

4. The syringe as claimed in claim 3, wherein said upwardly directed teeth being edges of detention rings made on said engagement member.

5. The syringe as claimed in claim 2, wherein said engagement means comprising a recessed ring with serrated periphery having upwardly directed sharp edges engaging said downwardly slanted edges of said retention means.

6. The syringe as claimed in claim 1, wherein the volume of said cylinder below said engagement zone being at least one milliliter.

7. The syringe as claimed in claim 2, wherein said cylinder comprising a further engagement zone close to said open end region of said cylinder, said further engagement designed similarly to said engagement zone to allow insertion of said plunger and to prevent withdrawal thereof one said plunger has been inserted.

8. A syringe as in claim 1, wherein said projecting member responsible for said tactile indication of the proximity of said plunger to said retention means is an annular rib or bead.

9. A syringe as in claim 1, further comprising a hypodermic needle connected to said hollow member.

10. A syringe as in claim 1, further comprising plunger withdrawal retention means positioned near said open end and configured to mate with said engagement member.

* * * * *